US005994064A

United States Patent [19]
Staub et al.

[11] Patent Number: 5,994,064
[45] Date of Patent: Nov. 30, 1999

[54] SIMPLE AND COMPLEX TANDEM REPEATS WITH DNA TYPING METHOD

[75] Inventors: Rick W. Staub, Sugarland; Michael G. Carrico, Missouri City, both of Tex.

[73] Assignee: Identigene, Inc., Houston, Tex.

[21] Appl. No.: 08/637,115

[22] Filed: Apr. 24, 1996

[51] Int. Cl.[6] .............................. C12Q 1/68; C07H 21/04; C12P 19/34
[52] U.S. Cl. ........................... 435/6; 435/91.2; 435/91.1; 536/24.3; 536/22.1
[58] Field of Search ................................. 435/91.2, 91.1, 435/6; 536/24.3, 22.1

[56] References Cited

U.S. PATENT DOCUMENTS 5,364,759   11/1994   Caskey .......................................... 435/6

OTHER PUBLICATIONS

Toda et al. Localization of a Gene for Fukuyame Type Congenital Muscular Dystrophy to Chromosome 9q31–33. Nature Genetics, vol. 5, pp. 283–286, 1993.
Alford R.L., et al.,*Am. J. Hum. Genet.,* 55(190):190–5 (1994).
Clayton T.M., et al., *Forens. Sci. Int'l,* 76:17–25 (1995).
Corach D, et al., *Electrophoresis,* 16:1617–23 (1995).
Edwards A., et al., *Am J. Hum. Genet.,* 49:746–56 (1991).
Evett I.W., et al., *Am. J. Hum. Genet.,* 58:398–407 (1996).
Gill P., et al., *Electrophoresis,* 16:1543–52 (1995).
Hammond H.A., et al., *Am. J. Hum. Genet.,* 55:175–89 (1994).
Holgersson S. et al., *Electrophoresis,* 15(7):890–5 (1994).
Huang N.E., et al., *Foren. Sci. Int'l,* 71:131–6 (1995).
Kimptom C. et al., *Foren. Sci. Int'l,* 71(2):137–52 (1995).
Kimpton C., et al., *in PCR Methods and Applications,* 13–22 (1993).
Moller A. & Brinkmann B., *Int. J. Legal Med.,* 106(5):262–7 (1994).
Puers C., et al., *Am. J. Hum. Gent.,* 53:000–000 (1993).
Sharma V. & Litt M., *Hum. Mol. Genet.,* 1:67 (1992).
Urquhart A., et al., *Int. J. Legal Med.,* 107:13–20 (1994).

*Primary Examiner*—Kenneth R. Horlick
*Assistant Examiner*—Joyce Tung
*Attorney, Agent, or Firm*—James Remenick; Baker & Botts, L.L.P.

[57] ABSTRACT

The present invention describes a process of DNA typing performed on human specimens utilizing a specific multiplex reaction which amplifies GATA short tandem repeats in the loci D18S535, D22S683, and D9S302 for the purpose of producing STR genotypes which may be used for identification purposes. This multiplex is an improvement over existing multiplex amplifications for STR typing in that it possesses an extremely high individualization potential for forensic studies and power of exclusion for parentage testing.

20 Claims, 8 Drawing Sheets

134 bp Allele:

TCATGTGACA AAAGCCACAC CCATAACTTT TTTCCTCTAG

ATAGACAGAT AGAT GATA GATA GATA GATA GATA GATA

GATA GATA GATA GATA TAGATTCTCT TTCTC TGCATTCTCA

TCTATATTTC TGTCT

FIGURE 2(A)

150 bp Allele:

TCATGTGACA AAAGCCACAC CCATAACTTT TTTCCTCTAG

ATAGACAGAT AGAT <u>GATA GATA GATA GATA GATA GATA</u>

<u>GATA GATA GATA GATA GATA GATA GATA GATA</u>

TAGATTCTCT TTCTC TGCATTCTCA TCTATATTTC TGTCT

FIGURE 2(B)

176 bp allele:

GGTGGAAATG CCTCATGTAG AAAAAAGGAA AGTTCTGATG

TTAGAAAGAG GGGGTCACCT TGAGAGAATG TGGACATGCT

GTCTGCTTTA TATA GATA GATA GATA GATA GATA GATA

GATA GATA GATA TAGATA TAGATA TAGATA TAGAT

TGTTTGTTTT GTTTTGTTTT GTT

FIGURE 3(A)

200 bp allele:

GGTGGAAATG CCTCATGTAG AAAAAAGGAA AGTTCTGATG TTAGAAAGAG GGGGTCACCT TGAGAGAATG TGGACATGCT GTCTGCTTTA TATA GATA GATA GATA GATA GATA GATA GATA GATA GATA GATA GATA GATA TAGATA TAGATA TAGATA TAGATA TAGATA TAGAT TGTTTGTTTT GTTTTGTTTT GTT

FIGURE 3(B)

262 bp allele:

A GATA GATA GATA GAT GATA GATA GATA GATA GATA GATA GATA GATA GATA GATA GAT GATA GATA GAT GATA GATA GATTA GATA GATA GATA GATA GATA GATA GATA GA GATA GAT GATA GAT GATA GGTAGGTA GATA GAT GATA GATA GATA GATA GATA GATA GGTA GATA GAT GATA GATA GATA GAT GATA GATA

FIGURE 4(A)

274 bp allele:

A GATA GATA GATA GATA GAT GATA GATA GATA GATA GATA GATA GATA GATA TAGAT GATA GATA GAT GATA GATA GATTA GATA GATA GATA GATA GATA GATA GATA GATA GA GATA GAT GATA GAT GATA GGTAGGTA GATA GAT GATA GATA GATA GATA GATA GATA GATA GATA GATA GATA GAT GATA GATA GATA GATGTTAGAT

FIGURE 4(B)

SIMPLE AND COMPLEX TANDEM REPEATS WITH DNA TYPING METHOD

BACKGROUND OF THE INVENTION

1. Field of the Invention

The present invention relates to a process of DNA typing using a multiplex amplification system of highly polymorphic simple or complex tandem repeat loci. These loci amplify robustly and cleanly in concert and provide a very powerful and quickly performed test which can be used in parentage, forensic, tissue origin, sample origin or genetic relatedness studies. The invention also relates to a new class of minisatellite called "complex tandem repeats" that displays more heterogeneity than simple tandem repeats and is of particular benefit in DNA typing applications.

2. Description of the Prior Art

Short tandem repeat (STR) polymorphisms are commonly used in DNA identification, either as adjuncts to other genetic tests, or as stand-alone tests. Typically, when STRs are used for human identification, they are amplified in groups of three to four loci (multiplex amplification). Generally, the resulting amplified fragments are analyzed by polyacrylamide gel electrophoresis. Polymorphisms are thus typed according to size by comparing to similarly labeled known external standards or differently labeled internal standards. U.S. Pat. No. 5,364,759 by Caskey, teaches the genus of simple tandem repeats as well as a DNA typing method employing the simple tandem repeats and PCR amplification of the loci. Fragments are analyzed by differential labeling of the products.

A critical parameter in DNA typing for paternity analysis is the power of exclusion for the system. Power of exclusion is the ability of a test to exclude a falsely accused man from paternity. Methods for computing the average (or expected) power of exclusion have been proposed (Chakravarti R. et al., Exclusion of Paternity: State of the Art., Am. J. Hu. Genet., 26:477–488 (1974); Garber R. A. & Morris J. W., General Equations for the Average Power of Exclusion for Genetic Systems of n Codominant Alleles in One-Parent and No-Parent Cases of Disputed Parentage, in Inclusion Probabilities in Parentage Testing, pp. 277–280 (1983); Chakravarti A. & Li C. C., The Effect of Linkage on Paternity Calculations, in Inclusion Probabilities in Parentage Testing, pp. 411–422 (1983)) and it can be estimated from gene frequency distributions of systems in Hardy-Weinberg equilibrium (Brenner C. & Morris. J. W., Paternity Index Calculations in Single Locus Hyper-Variable DNA Probes: Validation and Other Studies, Proceedings for The International Symposium on Human Identification, pp. 21–76 (1989)).

The commonly used STR multiplexes have exclusion probabilities in the range of 85% to 91% for paternity analysis. This compares unfavorably with restriction fragment length polymorphic loci (RFLP loci), which often provide an equivalent power with just one locus. Typically, at least three STR triplexes must be combined to provide sufficient exclusion power for most paternity trios. For example, Alford et al. describe a battery of nine STR loci amplified in 3 triplexes with an exclusion power of 99.75% in Caucasians (Alford R. L. et al., Rapid and Efficient Resolution of Parentage by Amplification of Short Tandem Repeats, Am. J Hum. Genet., 55:190–195 (1994)). Analysis of special cases in which the mother is not tested often results in low probabilities of paternity, even when ten of the commonly used STR systems are used. STR testing batteries which include greater numbers of lower power systems are more susceptible to this problem than are RFLP testing batteries which include a smaller number of higher power systems.

The low exclusion probabilities of commonly used STR loci are the most negative aspect of their use in paternity testing. This is not as serious a problem in forensic testing since the frequencies of both alleles of an individual are included in calculating match probabilities. In parentage testing however, only the frequency of the allele shared by the alleged parent and child is used in the probability calculation. Thus, although it is simpler and faster to perform DNA typing with STR loci than with RFLP loci and it can be performed with much smaller quantities of DNA, many laboratories are reluctant to make the switch because of this sacrifice in exclusion power.

Another disadvantage of current STR multiplex DNA typing systems is that the amplification is rarely, if ever, clean. In other words there is considerable formation of spurious bands, which is thought to be due to DNA polymerase slippage and mis-priming events (see e.g., Tautz D., Hyper variability of Simple Sequences as a General Source for Polymorphic DNA Markers, Nuc. Acids Res., 17(16) 6463–70 (1989)).

These and other disadvantages of the prior art are overcome by the present invention, and a method for DNA typing by multiplex amplification of highly polymorphic micro-satellite loci is provided.

SUMMARY OF THE INVENTION

In accordance with the present invention, a very powerful method of DNA typing is provided. More specifically, the invention relates to multiplex amplification of the D18S535, D22S683 and D9S302 tandem repeat loci of DNA. The amplification may be performed with primers of SEQ. ID. NOS. 1, 2, 3, 4, 5, and 6. If these primers are employed, then preferentially the template DNA is about 0.05 to 0.5 ng/$\mu$l and the magnesium concentration is about 0.5 to 1.2 mM. Primer concentrations may be about 0.1 to 1.0 $\mu$M for SEQ. ID. NOS. 1, 2, 3, 4, 5 and 6. Most preferentially, the DNA is at 0.2 ng/$\mu$l, the magnesium at 0.8 mM and the primers at 0.4 $\mu$M for SEQ. ID. NOS. 1,2, 5 and 6, and about 0.6 $\mu$M for SEQ. ID. NOS. 3 and 4.

In another embodiment of the invention, a method of DNA typing comprising multiplex amplification of a locus selected from the group consisting of the D18S535, D22S683 and D9S302 loci is provided.

In yet another embodiment, a method of DNA typing comprising multiplex amplification of two loci selected from the group consisting of the D18S535, D22S683 and D9S302 loci is provided.

In a fourth embodiment, a method of DNA typing comprising multiplex amplification of complex tandem repeats is provided. The complex tandem repeats may be selected from the group consisting of D9S302, D22S683, D7S1804, D2S1780, D3S2387 and D2S1326 Loci. Preferably, the complex tandem repeats have a heterozygosity of 87% to 97% and/or contain a GATA motif. Preferably, the multiplex amplification of three complex tandem repeats has an exclusionary power of 97.0% to 99.5% and most preferably, from 99.9% to 99.99%.

These and other advantages of the present invention will become apparent from the following detailed description.

BRIEF DESCRIPTION OF THE DRAWINGS

FIG. 2(a) is the sequence of the 134 bp D18S535 allele.
FIG. 2(b) is the sequence of the 150 bp D18S535 allele.
FIG. 3(a) is the sequence of the 176 bp D22S683 allele.
FIG. 3(b) is the sequence of the 200 bp D22S683 allele.
FIG. 4(a) is the sequence of the 262 bp D9S302 allele.
FIG. 4(b) is the sequence of the 274 bp D9S302 allele.

DETAILED DESCRIPTION OF THE INVENTION

Figure 1A:
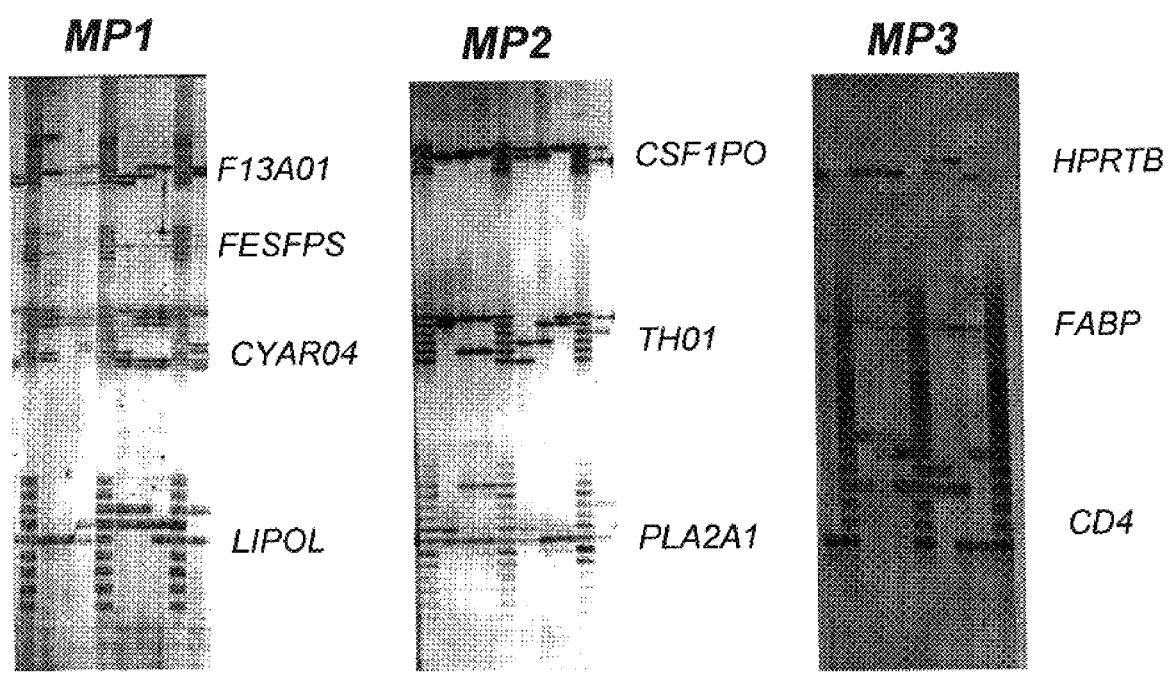
FIG. 1(a) depicts an example of three STR amplification performed with previously available technology.

The invention disclosed herein comprises performing multiplex amplification on the loci selected from the group consisting of D9S302, D22S683, and D18S535. In an alternative embodiment, the invention comprises performing multiplex amplification of any combination of the D9S302, D22S683, and D18S535 and other loci, such as D7S1804, D2S1780, D3S2387 and D2S1326.

In yet another embodiment, a new class of extremely polymorphic loci, termed herein "complex tandem repeats," are provided for DNA typing analyses. There are two classes of CTR's provided herein. Class I consists of dual tandem repeats where one type of repeat is followed by a second type of repeat. Class II consists of islands of a simple repeat separated by short sections of non-repeat sections.

The method for DNA typing as described herein can be used in many applications including, but not limited to, parentage testing, determination of tissue or sample origin, genetic relatedness studies, genetic mapping, zygosity testing in twins, evaluating bone marrow transplantations, and quality control of cultured cells. The method can also be used for many forensic applications including identification of degraded or minute samples, and the analysis of mixed samples, such as are commonly found in rape cases.

Generally, suitable template DNA will be genomic DNA, or any DNA sufficiently intact to provide at least one DNA molecule with the locus of interest intact. RNA samples that span the locus of interest may also be amplified by first converting the RNA to cDNA or by any of the techniques well known to those of skill in the art. Although the embodiments described herein employ human genomic DNA as a template DNA, it is possible that complex tandem repeats from other species will be found or that the complex tandem repeats or their flanking sequences might be conserved between species. Thus, the method of DNA typing described herein is not restricted to human applications, but may be used in plant and animal breeding and pedigree analysis.

Any suitable amplification procedure known to those skilled in the art, such as, but not limited to, polymerase chain reaction (PCR), Qβ replication, isothermal sequence replication, or ligase chain reaction may be used. However, the most developed and well understood amplification systems are PCR systems. Thus, PCR is currently the preferred method of amplification.

Multiplex amplification of different loci requires loci specific reaction conditions and procedures. In general, optimization of multiplex amplification may be difficult, but can be achieved by systematic variation of each parameter in the reaction. A Taguchi array (a statistical means of minimizing the number of samples required to systematically vary each parameter of an experiment) can be used to minimize the number of variants that must be tested to achieve optimization (Taguchi G., *Reports Statist. Appl. Res.* 7:1 (1960)). The multiplex employed herein behaved in a unique and unusual fashion with respect to certain parameters, such as annealing temperature, and its optimization is described in more detail in Example 3.

The invention provides a significant improvement in exclusion power over the presently used and commercially available STR multiplexes. The D9S302/D22S683/D18S535 multiplex has an exclusion probability of 99.1% for African Americans, which is significantly higher than any other STR triplex currently available. All other STR triplexes and quadriplexes currently used for paternity analysis have exclusion powers ranging from 85% to 91% (e.g., HUMF13AO1/HUMFESFPS/HUMCYARO4/HUMLIPOL, HUMCSFIPO/HUMTHO1/HUMPLAZA1, and HUMHPRTB/HUMFABP/HUMCD4). Only the D12S1090/D3S1744/D18S849 triplex approaches the described triplex in exclusion power. The D12S1090/D3S1744/D18S849 triplex has a 96.9% power of exclusion for Caucasians and a 97.4% power of exclusion for African Americans, Hispanics and Asians.

Two of the loci described herein, D9S302 (D9) and D22S683 (D22), are more accurately described as "complex" tandem repeats than as simple tandem repeats. These loci are more complex than a simple head to tail repeat of a 2–7 nucleotide sequence. D22 is a Class I CTR and consists of a stretch of tandemly repeated GATAs followed by a stretch of TAGATA tandem repeats. Thus, variability is present in the number of GATA repeats as well as the number of TAGATA repeats. The additional level of complexity of this locus probably accounts for its high degree of heterozygosity (88%–94%).

D9 is a class II CTR and is even more complex, containing GATA repeats interspersed with a variety of sequences, including GAT, GATT, TAGAT, and more complicated variations. This high level of complexity is reflected by a very high heterozygosity (90%–93%) and contributes greatly to the exclusion power of the system.

These complex loci are named "complex tandem repeats" (CTR) herein and present a new type of loci of particular benefit in DNA typing. The higher degree of variability within the loci is reflected by higher heterozygosity in the population and thus allows a higher exclusion power than typical STR loci. A third CTR of the complexity demonstrated by D9 and D22 would present an exclusion power of approximately 99.4% when used in a triplex amplification with D9 and D22. A quadriplex of CTR loci could present an exclusion power of 99.9%.

CTR loci were not generally recognized as being of particular benefit in DNA typing analysis prior to this invention. However, a single locus, the SE33 or ACTBP2 locus, commonly used in forensic analysis, was known to have sequence complexity and a high degree of heterozygosity (96% in Swedes). We now recognize that the SE33 locus is a Class II CTR according to the definitions used herein (Moller A., Brinkmann B., Sequencing Data Reveal Considerable Polymorphism, *Int. J. Legal Med.*, 106(5):262–7 (1994); Holgerson S. et al., Fluorescent-Based Typing of the Two Short Tandem Repeat Loci HUMTH01 and HUMACTBP2: Reproducibility of Size Measurements and Genetic Variation in the Swedish Population, *Electrophoresis*, 15(7):890–5 (1994)).

It was recognized that simple STR systems were readily amenable to multiplex PCR, but that more complex sequences "presented difficulties" (Kimptom C. et al., Report on the Second EDNAP Collaborative STR Exercise, *Forensic Sci. Int.*, 71(2):137–52 (1995)). We have confirmed that not all loci are equally amenable to multiplex amplification. For example, certain GGAA repeats were impossible to amplify cleanly without the production of numerous artifactual bands, produced presumably by slippage during the amplification process or non-specific amplification. We attempted to multiplex D20S470, D3S2387, and D14S617 as a triplex or D20S470, D4S2431, D3S2387 and D14S617 as a quadriplex. We altered the DNA concentration, $MgCl_2$ concentration, and primer concentrations. None of these steps helped to improve the reaction specificity or robustness. Other loci that we attempted to use in a second multiplex that also failed were D1S1656 and D1S1612. Numerous attempts to optimize the multiplex amplification for these repeats resulted in failure and these loci were eventually abandoned.

In contrast, we have discovered that it is possible to obtain very clean and reproducible results for the co-amplification of complex GATA (and its variants) repeats. Additional CTRs based on variations of the GATA repeat can be successfully used in this system, including, but not limited to, D7S 1804 (GenBank Accession No. G08619), D2S 1788 (GenBank Accession No. G08006), D3S2387 (GenBank Accession No. G08236) and D2S1326 (GenBank Accession No. G08136).

Contrary to standard teaching in the art, it is not necessary that the primers be of approximately equivalent GC content. It has been demonstrated that primers of GC content ranging from 22% to 60% will function together to provide a clean multiplex amplification (see SEQ. ID. NOS. 1–6).

Also contrary to expectation, when attempting to optimize our described multiplex, raising the annealing temperature increased, rather than decreased, the level of spurious band formation. This may be due to improper priming of DNA polymerase at slightly higher temperatures. Best results were obtained with lower annealing temperatures as indicated in the examples herein.

Furthermore, we discovered that the reaction conditions suggested by the suppliers of the primers were less than optimal for multiplex amplification. The reaction conditions suggested for the Cooperative Human Linkage Center (CHLC) markers (non-radioactive) were as follows: For a 8.35 $\mu$l reaction; 40.0 ng DNA, 3.0 $\mu$M each dNTP, 1.5 Taq polymerase buffer, 0.25 U Taq, 0.3 $\mu$M each primer. The PCR profile was as follows: 3 min at 94° C., 35 cycles of 30 sec at 94° C., 30 sec at 55° C., 30 sec at 72° C. We attempted our usual lab protocol first and it failed. Then we tried the recommended protocol and it did not work either.

However, the accurate titration of both magnesium and template DNA levels was discovered to greatly improve results. These two parameters were critical for high quality amplification and optimal conditions for the three loci described herein were 0.05 to 0.5 ng/$\mu$l template DNA, preferably 0.2 ng/$\mu$l, and 0.5 to 1.2 mM magnesium, preferably 0.8 mM. Other critical parameters for high quality amplification were primer annealing temperature (which was optimized at 55–60° C., preferably at 58° C.), reaction volume (which was optimized at 20–30 $\mu$l, preferably at 25 $\mu$l), and primer concentration ( 0.1 to 1.0 $\mu$M for SEQ. ID. NOS. 1, 2, 3, 4, 5 and 6, preferably 0.4 $\mu$M for SEQ. ID. NOS. 1, 2, 5 and 6, and 0.6 $\mu$M for SEQ. ID. NOS. 3 and 4). Unlike many, if not all of the prior art multiplex STRs, the system described herein provided very clean results, producing only the fragments of interest. No significant spurious bands were formed, allowing for simple and accurate genotyping.

The purpose of multiplex amplification of these loci was to determine the sample's genotype for the loci involved. This genotype can be described in various ways, including sizes of amplified fragments in nucleotide pairs, number of tandem GATA repeats, or number of GATA equivalents if the population variability is caused by complex GATA repeats.

The sequence heterogeneity of the loci may be detected in any of several ways. In this system, it is technically very simple to determine the genotype according to the size of the amplified repeat as demonstrated in the examples herein. Here the fragments are separated by polyacrylamide gel electrophoresis, stained with $AgNO_3$, and sizes determined by comparison to standards. The DNA may be visualized in a number of ways, including, but not limited to, radiolabeling, fluorescent labeling, color staining, and chemiluminescent detection.

In order to determine genotype by size, it was necessary to choose primers to yield a series of nonoverlapping fragments for the three loci. The oligonucleotide primers which flank these loci were developed by researchers at the CHLC and the sequences were obtained from the GenBank (Accession Nos. G08746, G08086, and G07985). It will be appreciated by those of ordinary skill in the art that the primers defining these polymorphic microsatellites can be manipulated to change either the reaction conditions and/or the size of the fragments amplified.

There are many additional procedures that can be used to determine the genotype of the amplified locus, including, but not limited to, sequencing of the fragment, ASO hybridization, and capillary electrophoresis.

To one skilled in the art it will be apparent that the invention disclosed herein is an improvement over previously described STR multiplexes. The multiplex has an extremely high power of individualization in the four major racial groups. The loci co-amplify cleanly and robustly, enabling accurate genotyping of the three loci using very small quantities of DNA. Presently, paternity testing employing these three loci has the power to exclude 99.1% of falsely accused men. Additionally, the use of this triplex and another triplex of comparable power would enable the exclusion of 99.99% of non-fathers and would necessitate running the minimal number of polyacrylamide gels for analysis of data. This would greatly reduce technical labor involved in human identification analyses and, at the same time, significantly increase the power of the testing.

The following examples serve to illustrate specific embodiments of the invention, but should not be considered as a limitation on the scope of the invention.

EXAMPLE 1

Polymorphic Loci

This example describes the three loci and primers suitable for their amplification.

D18S535

The chromosomal location was 18q12.2–12.3. The forward primer was 20 nucleotides long, and its sequence was:

5' TCATGTGACAAAAGCCACAC 3' (SEQ. ID. NO. 1).

The reverse primer was 25 nucleotides long, and its sequence was:

5' AGACAGAAATATAGATGAGAATGCA 3' (SEQ. ID. NO. 2).

The size range of fragments found in over 800 humans is 122 to 158 base pairs.

D22S683

D22S683 has been localized only to chromosome 22. The forward primer was 23 nucleotides long, and its sequence was:

5' AACAAAACAAAACAAAACAAACA 3' (SEQ. ID. NO. 3).

The reverse primer was 20 nucleotides long, and its sequence was:

5' GGTGGAAATGCCTCATGTAG 3' (SEQ. ID. NO.4).

The size range of fragments found in over 800 humans was 162 to 226 base pairs.

D9S302

The chromosomal location of D9S302 is 9q31–q33. The primers used in the amplification reaction were both 20 nucleotides long. The sequence of the forward primer was:

5' GGGGACAGACTCCAGATACC 3' (SEQ. ID. NO.5), and the sequence of the reverse primer was:

5' GCGACAGAGTGAAACCTTGT 3' (SEQ. ID. NO. 6).

The size range of fragments found in over 800 humans was 236 to 364 base pairs.

EXAMPLE 2

Multiplex PCR

This sample describes optimal amplification conditions for the three loci. Five to ten nanograms of genomic DNA were amplified in a Perkin Elmer 9600 thermal cycler in a 25 μl reaction. The other components of each reaction were 10 mM Tris-HCl, pH 8.3; 50 mM KCl; 0.8 mM MgCl$_2$; 0.01% gelatin; 200 μM of each deoxynucleoside triphosphate; 1.25 Units of AmpliTaq DNA Polymerase.

Primer concentrations were arbitrarily determined at 20 pmol per reaction. Comparing the intensity of each locus on silver-stained polyacrylamide sequencing gels enabled determination of optimal primer concentrations. The optimal primer amounts were 10 pmol (0.4 mM) for D9S302 and D18S535 and 15 pmol (0.6 mM) for D22S683 per reaction.

The PCR conditions for this multiplex were: an initial hold at 94.5° C. for 2.5 minutes; 30 cycles of 95° C. for 45 seconds, 58° C. for 1 minute, and 72° C. for 1 minute; a hold of 72° C. for 7 minutes; and a final hold at 15° C.

Figure 1B:
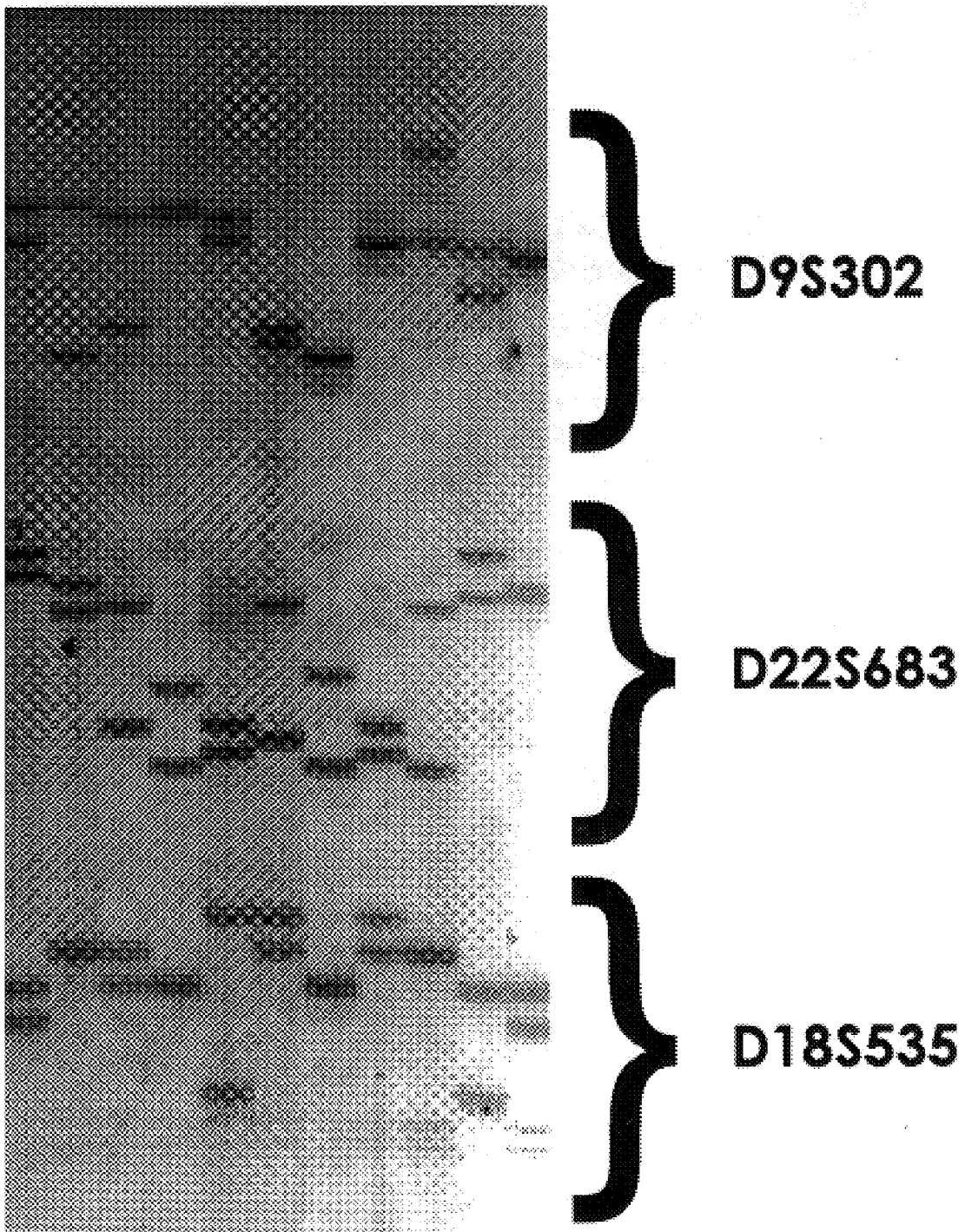
FIG. 1(b) is an example of eleven different individuals typed with the D9S302, D22S683, and D18S535 loci.

FIG. 1 compares prior art technology with that of the present invention. FIG. 1A shows three prior art STR multiplexes that are commonly used in DNA typing. The indicated loci were amplified, separated by sequencing gel and stained with silver nitrate. Multiplex one (MP 1) was F13A01/FESFPS/CYAR04/LIPOL and had a power of exclusion of 91.6%. MP2 was CSF1PO/TH01/PLA2A1 and had a power of exclusion of 89.4%. MP3 was HPRTB/FABP/CD4 and had a power of exclusion of 85.3%. A large number of spurious bands complicates the analyses of these gels. In contrast, very clear and unambiguous results are seen in FIG. 1B with the loci of this invention. The D9S302/D22S683/D18S535 triplex amplified cleanly and robustly and provided a power of exclusion of 98.4%.

EXAMPLE 3

Determining STR Genotypes and Population Variability of Fragment Size

This example describes the genotype variability at these three loci present in the four major racial groups (Caucasian, African American, Asian and Hispanic). Amplified products, diluted 2 to 1 with formamide loading buffer, were electrophoresed through a 4% /1X TBE denaturing polyacrylamide gel (19:1 acrylamide:bisacrylamide, 7.5 M urea) for 70 minutes at 90W constant power in a S2 sequencing gel apparatus (BRL-LTI). Next, the plates were separated and the gels were stained with silver nitrate and developed in sodium carbonate. Gels were left out overnight to dry and photographs were taken with LOD7 duplicating film (3M).

Allele calls were determined by comparing the unknown typing to Centre d'Etude Polymorphism Humane (CEPH) samples 1331-01 and 1331-02 (see FIG. 1). Allele sizes for these samples were obtained from gene mapping researchers at the Cooperative Human Linkage Center (CHLC). For the population database gels, Biolmage Whole Band Analysis Software was used to assist in making allele calls in base pairs since exact numbers of GATA repeats were not known at the time. Allelic ladders are being developed to facilitate the analysis of each unknown sample. Bands in allelic ladder constructions will be spaced one full GATA (or GATA equivalent) repeat apart to be used in genotyping by comparing gel migration of these known fragments with that of specimens of unknown genotype.

The African American and Caucasian specimens used in the databasing were parents from paternity analyses previously performed in this laboratory. Only unrelated specimens were used. Blood specimens from Asians and Hispanics were obtained from the Houston Blood Center. Approximately 200 (400 alleles) samples of each race were amplified and analyzed. Data are presented in the following tables. Table 1 shows the allele frequencies for the CTR locus D9S302. All alleles are expressed as amplified fragment size in base pairs. Table 2 shows the allele frequencies for the CTR locus D22S683. All alleles are expressed as amplified fragment size in base pairs and translated into GATA equivalents as described in Example 4. Likewise, in Table 3 the allele frequencies for the STR locus D1 8S535 are shown. All alleles are expressed as amplified fragment size in base pairs and are translated into GATA repeats as described in Example 4.

TABLE 1

D9S302 ALLELE FREQUENCIES

| ALLELE (BP) | AFRICAN AMERICAN | CAUCASIAN | HISPANIC | ASIAN |
|---|---|---|---|---|
| 220 | 0.000 | 0.000 | 0.000 | 0.002 |
| 236 | 0.000 | 0.000 | 0.000 | 0.002 |
| 242 | 0.000 | 0.000 | 0.004 | 0.000 |
| 244 | 0.000 | 0.000 | 0.000 | 0.002 |
| 246 | 0.000 | 0.000 | 0.007 | 0.000 |
| 248 | 0.000 | 0.007 | 0.000 | 0.000 |
| 250 | 0.003 | 0.005 | 0.002 | 0.000 |
| 252 | 0.000 | 0.000 | 0.000 | 0.002 |
| 254 | 0.003 | 0.005 | 0.000 | 0.000 |
| 256 | 0.005 | 0.000 | 0.002 | 0.002 |
| 258 | 0.023 | 0.063 | 0.029 | 0.033 |
| 260 | 0.008 | 0.000 | 0.002 | 0.002 |
| 262 | 0.048 | 0.107 | 0.060 | 0.062 |
| 264 | 0.000 | 0.012 | 0.000 | 0.002 |
| 266 | 0.082 | 0.187 | 0.188 | 0.098 |
| 268 | 0.013 | 0.002 | 0.002 | 0.010 |
| 270 | 0.028 | 0.150 | 0.201 | 0.079 |
| 272 | 0.010 | 0.002 | 0.000 | 0.002 |
| 274 | 0.015 | 0.035 | 0.044 | 0.024 |
| 276 | 0.010 | 0.009 | 0.007 | 0.005 |
| 278 | 0.010 | 0.002 | 0.007 | 0.010 |
| 280 | 0.015 | 0.005 | 0.020 | 0.019 |
| 282 | 0.013 | 0.000 | 0.007 | 0.005 |
| 284 | 0.015 | 0.026 | 0.046 | 0.071 |
| 286 | 0.015 | 0.007 | 0.024 | 0.005 |
| 288 | 0.071 | 0.054 | 0.055 | 0.076 |
| 290 | 0.028 | 0.021 | 0.033 | 0.012 |
| 292 | 0.105 | 0.040 | 0.066 | 0.107 |
| 294 | 0.015 | 0.002 | 0.007 | 0.007 |
| 296 | 0.179 | 0.072 | 0.040 | 0.105 |
| 298 | 0.003 | 0.002 | 0.000 | 0.000 |
| 300 | 0.120 | 0.058 | 0.044 | 0.002 |

TABLE 1-continued

D9S302 ALLELE FREQUENCIES

| ALLELE (BP) | AFRICAN AMERICAN | CAUCASIAN | HISPANIC | ASIAN |
|---|---|---|---|---|
| 302 | 0.005 | 0.007 | 0.002 | 0.002 |
| 304 | 0.071 | 0.056 | 0.051 | 0.062 |
| 306 | 0.005 | 0.002 | 0.000 | 0.002 |
| 308 | 0.028 | 0.021 | 0.031 | 0.048 |
| 310 | 0.000 | 0.000 | 0.000 | 0.005 |
| 312 | 0.018 | 0.012 | 0.009 | 0.029 |
| 314 | 0.000 | 0.005 | 0.000 | 0.000 |
| 316 | 0.005 | 0.016 | 0.004 | 0.010 |
| 318 | 0.000 | 0.000 | 0.000 | 0.000 |
| 320 | 0.000 | 0.005 | 0.000 | 0.005 |
| 324 | 0.000 | 0.002 | 0.004 | 0.000 |
| 328 | 0.003 | 0.000 | 0.000 | 0.000 |
| 332 | 0.003 | 0.000 | 0.000 | 0.000 |
| 336 | 0.003 | 0.000 | 0.000 | 0.000 |
| 364 | 0.003 | 0.000 | 0.000 | 0.000 |
| TOTALS | 1.000 | 1.000 | 1.000 | 1.000 |
| N(alleles) | 392 | 428 | 452 | 420 |

TABLE 2

D22S683 ALLELE FREQUENCIES

| ALLELE (BP) | GATA EQUIVALENTS | AFRICAN AMERICAN | CAUCASIAN | HISPANIC | ASIAN |
|---|---|---|---|---|---|
| 162 | 10 | 0.003 | 0.000 | 0.000 | 0.002 |
| 164 | 10.2 | 0.000 | 0.000 | 0.002 | 0.002 |
| 166 | 11 | 0.000 | 0.000 | 0.002 | 0.000 |
| 168 | 12.2 | 0.028 | 0.000 | 0.063 | 0.220 |
| 170 | 12 | 0.000 | 0.000 | 0.005 | 0.220 |
| 172 | 12.2 | 0.008 | 0.030 | 0.021 | 0.032 |
| 174 | 13 | 0.008 | 0.086 | 0.089 | 0.083 |
| 176 | 13.2 | 0.103 | 0.154 | 0.087 | 0.032 |
| 177 | 13.3 | 0.003 | 0.000 | 0.000 | 0.000 |
| 178 | 14 | 0.082 | 0.192 | 0.190 | 0.227 |
| 180 | 14.2 | 0.080 | 0.110 | 0.230 | 0.061 |
| 182 | 15 | 0.018 | 0.044 | 0.040 | 0.054 |
| 184 | 15.2 | 0.052 | 0.044 | 0.052 | 0.066 |
| 185 | 15.3 | 0.003 | 0.000 | 0.000 | 0.000 |
| 186 | 16 | 0.021 | 0.009 | 0.016 | 0.017 |
| 187 | 16.1 | 0.003 | 0.000 | 0.000 | 0.000 |
| 188 | 16.2 | 0.028 | 0.042 | 0.052 | 0.032 |
| 189 | 16.3 | 0.005 | 0.000 | 0.000 | 0.000 |
| 190 | 17 | 0.021 | 0.005 | 0.016 | 0.005 |
| 192 | 17.2 | 0.028 | 0.026 | 0.009 | 0.005 |
| 193 | 17.3 | 0.003 | 0.000 | 0.000 | 0.000 |
| 194 | 18 | 0.021 | 0.037 | 0.016 | 0.022 |
| 195 | 18.1 | 0.008 | 0.000 | 0.000 | 0.000 |
| 196 | 18.2 | 0.023 | 0.009 | 0.005 | 0.000 |
| 198 | 19 | 0.021 | 0.054 | 0.040 | 0.056 |
| 199 | 19.1 | 0.021 | 0.002 | 0.000 | 0.000 |
| 200 | 19.2 | 0.137 | 0.009 | 0.012 | 0.020 |
| 201 | 19.3 | 0.026 | 0.000 | 0.000 | 0.000 |
| 202 | 20 | 0.046 | 0.016 | 0.021 | 0.029 |
| 203 | 20.1 | 0.005 | 0.000 | 0.000 | 0.000 |
| 204 | 20.2 | 0.049 | 0.009 | 0.012 | 0.010 |
| 205 | 20.3 | 0.018 | 0.000 | 0.000 | 0.000 |
| 206 | 21 | 0.021 | 0.000 | 0.012 | 0.000 |
| 207 | 21.1 | 0.005 | 0.000 | 0.000 | 0.000 |
| 208 | 21.2 | 0.026 | 0.002 | 0.000 | 0.010 |
| 209 | 21.3 | 0.008 | 0.000 | 0.000 | 0.000 |
| 210 | 22 | 0.036 | 0.000 | 0.007 | 0.005 |
| 211 | 22.1 | 0.008 | 0.000 | 0.000 | 0.000 |
| 212 | 22.2 | 0.018 | 0.000 | 0.000 | 0.000 |
| 214 | 23 | 0.003 | 0.000 | 0.000 | 0.000 |
| 216 | 23.2 | 0.003 | 0.000 | 0.000 | 0.000 |
| 220 | 24.2 | 0.003 | 0.000 | 0.000 | 0.000 |
| 226 | 26 | 0.003 | 0.000 | 0.000 | 0.000 |
| TOTALS | | 1.000 | 1.000 | 1.000 | 1.000 |
| N(alleles) | | 388 | 428 | 426 | 410 |

TABLE 3

D18S535 ALLELE FREQUENCIES

| ALLELE (BP) | GATA REPEATS | AFRICAN AMERICAN | CAUCASIAN | HISPANIC | ASIAN |
|---|---|---|---|---|---|
| 122 | 7 | 0.000 | 0.000 | 0.002 | 0.000 |
| 126 | 8 | 0.003 | 0.000 | 0.000 | 0.000 |
| 130 | 9 | 0.008 | 0.113 | 0.042 | 0.139 |
| 134 | 10 | 0.028 | 0.012 | 0.005 | 0.015 |
| 138 | 11 | 0.125 | 0.023 | 0.028 | 0.032 |
| 142 | 12 | 0.242 | 0.190 | 0.178 | 0.144 |
| 146 | 13 | 0.286 | 0.319 | 0.329 | 0.278 |
| 150 | 14 | 0.204 | 0.204 | 0.294 | 0.259 |
| 154 | 15 | 0.099 | 0.134 | 0.109 | 0.120 |
| 158 | 16 | 0.005 | 0.005 | 0.014 | 0.015 |
| TOTALS | | 1.000 | 1.000 | 1.000 | 1.000 |
| N(alleles) | | 392 | 426 | 432 | 410 |

EXAMPLE 4

DNA Sequencing of Selected Alleles

This example describes the sequencing and data obtained from the three loci.

Isolation of Alleles for Sequence Analysis

Heterozygous samples with alleles to be sequenced were chosen from the original database gel photographs. Amplified products were re-run on polyacrylamide gels. After silver staining, the alleles of interest were removed from the stained gel with a scalpel. The gel fragments were then placed in individual microcentrifuge tubes and submerged in approximately 25 μL, of sterile ultrapure H$_2$O for 12 hours. 5 μL aliquots of this solution were then placed in four 0.2 ml MicroAmp tubes (Perkin Elmer). All other PCR reaction components were then added and the alleles were amplified using the conditions described above for multiplex PCR, except only the primers for the system of interest were added.

After completion of thermal cycling, tubes of each allele were pooled and 10 μL were run on 4% NuSieve agarose gels (FMC), and stained with ethidium bromide to check for proper amplification. Amplification products were then sequenced by performing cycle sequencing (re-amplification of amplified fragments using only one of the original primers in a sequencing reaction containing ddNTPs) of both strands until the opposite primer region is reached. The fragment sequence is then determined by matching complementary regions of these sequences and meshing the primer sequences.

D18S535 Allele Sequences

A 134 bp and a 150 bp allele were isolated from sample F1938 (African American male), and sequenced as described above. In FIG. 2, the DNA sequences (5'→3') of the 134 bp and 150 bp allelic PCR fragments for D18S535 are shown as defined by the primers (underlined). The fragments differed only by the number of GATA repeats (bold, double underline) they possessed. The two alleles had variable GATA STR regions with the 150 bp fragment possessing 14 GATA repeats and the 134 bp fragment possessing 10 GATA repeats. The flanking regions in the two alleles were identical. Since no alleles were observed that did not differ from other alleles by multiples of 4 bp, it is likely that the population variability observed for this STR locus was entirely due to differences in number of GATA repeats.

D22S683 Allele Sequences

A 176 bp allele was isolated from specimen F1572 (African American male) and a 200 bp allele was isolated from specimen B7 (African American male) as described above. Both alleles were sequenced as described above. In FIG. 3, the DNA sequences (5'→3') of the 176 bp and 200 bp allelic amplified fragments of the D22S683 locus are shown with the primer sequences underlined. The flanking sequences of these two alleles were identical. The difference in size of the two fragments is accounted for by variability in repeat number of two adjacent regions (double underline): a GATA repeat region (bold) and a TAGATA repeat region (bold, shadowed). This type of variability is termed herein a Class I CTR and provides a far greater amount of polymorphism at the population level, as evidenced by the data collected for the four major racial groups in the United States.

In order to describe these alleles more conveniently, it was decided to name them by their GATA-equivalents. For example, an allele with the composition [GATA]$_9$ [TAGATA]$_2$ would be indistinguishable from a [GATA]$_{12}$ allele and would be called a 12 repeat allele. Using accepted nomenclature, the 176 bp allele would be called a 13.2 repeat allele (13 full GATA repeat equivalents plus 2 bp), and the 200 bp allele would be called a 19.2 allele.

Interestingly, there were some alleles discovered in the population database that differ from the full and half repeat alleles by one base pair. It is not yet clear where this variability arises at the nucleotide level, but it is easily detectable on sequencing gels. Thus, the complex tandem repeat D22S683 shows an extremely high degree of population variability at the nucleotide level, making it a powerful component of the multiplex described herein.

D9S302 Allele Sequences

A 262 bp allele was isolated from specimen M1900 (African American female) and a 274 bp allele was isolated from specimen F 1453 (African American male). Because of their larger size only partial sequences of the D9S302 amplicon have been obtained by the cycle sequencing technique described above. These partial sequences are shown in FIG. 4. In FIG. 4, the DNA sequences (5'→3') of the 262 bp and 274 bp allelic amplified fragments for D9S302 are shown. The flanking sequences remain undetermined. GATA sequences are shown in bold, double underlined font. It is apparent from the partial sequences of the 262 bp and 274 bp alleles that there were two to several GATA tandem repeat regions separated by non-GATA sequences. This GATA repeat region is termed herein a Class II CTR and it displayed a high level of population variability, as did the D22S683 complex repeat region described above. When the actual number of GATA repeats are determined, alleles will be described by how many repeats they contain. They were described herein simply by the size of the allelic fragments in base pairs for the purpose of performing population genetic tests on the three loci which comprise the multiplex.

EXAMPLE 5

Computations and Statistics

DNA specimens from several family pedigrees were amplified for the D9S302/D22S683/D18S535 multiplex and demonstrated Mendelian inheritance. From the other specimens (>800) that were typed and databased for the four major racial groups, exact tests, likelihood ratio tests, and a test based on total heterozygosity were performed to determine that the population allele distributions did not differ significantly from Hardy-Weinberg expectations. To test for variance across loci, interclass correlations were computed for the variance in number of heterozygous loci. No significant variance from Hardy-Weinberg expectations were revealed, either within or between loci. Thus, these loci show no evidence of population heterogeneity within loci and are independent of one another. Hence, the multiplication rule applies for computing match probabilities.

TABLE 4

| | AFRICAN AMERICAN | CAUCASIAN | HISPANIC | ASIAN |
|---|---|---|---|---|
| D9S302 | | | | |
| # of individuals Heterozygotes | 196 | 214 | 226 | 210 |
| Observed (%) | 91.33 | 91.12 | 86.73 | 90.95 |
| Exp. ± SE (%) | 92.0 ± 1.9 | 90.9 ± 2.0 | 90.1 ± 2.0 | 93.1 ± 1.7 |
| D22S683 | | | | |
| # of individuals Heterozygotes | 194 | 214 | 213 | 205 |
| Observed (%) | 91.75 | 87.85 | 89.67 | 88.78 |
| Exp. ± SE(%) | 93.8 ± 1.7 | 89.6 ± 2.1 | 88.3 ± 2.2 | 87.6 ± 2.3 |
| D18S535 | | | | |
| # of individuals Heterozygotes | 196 | 213 | 216 | 205 |
| Observed (%) | 78.57 | 78.87 | 75.93 | 78.54 |
| Exp. ± SE (%) | 79.4 ± 2.9 | 79.3 ± 2.8 | 76.1 ± 2.9 | 80.2 ± 2.8 |
| TOTAL Indiv. AVERAGE HET. | 586 | 641 | 655 | 620 |
| Observed (%) | 87.20 | 85.96 | 84.12 | 86.13 |
| Exp. ± SE(%) | 88.4 ± 1.3 | 86.6 ± 1.3 | 84.9 ± 1.4 | 87.0 ± 1.3 |

Table 4 shows the heterozygosity values for all three loci in the four major races. The close agreement between observed and expected values indicated the populations were in Hardy Weinberg equilibrium. It also served to illustrate the high degree of polymorphism displayed by these three loci as evidenced by their high levels of heterozygosity. Interestingly, the level of heterozygosity was higher than was indicated in the Research Genetics catalogue (1995) (D9–90%, D22–90% and D18–76%). The reasons for underestimating the heterozygosity of these loci is not clear.

All three loci combined to provide a power of exclusion for paternity testing of 99.1 % for African Americans, 98.4% for Caucasians, 97.7% for Hispanics, and 98.5% for Asians for forensic testing. The match probabilities calculated for the most frequent genotypes were $1/150,000$ for African Americans, $1/44,400$ for Caucasians, $1/24,500$ for Hispanics and $1/57,000$ for Asians. Commercially available STR multiplex kits display far inferior match probabilities, ranging from $1/424$ for the CSFIPO/TPOX/THO1 triplex in Caucasians to $1/25,575$ for the CSFIPO/TPOX/THO1/vWA quadriplex in African Americans (available from Promega). Thus, this multiplex provided a powerful test battery for forensic testing and a very potent, fast, and efficient identity test.

The frequencies of the most common genotypes for all three systems in the four major racial groups are shown in Table 5. Frequencies of the most common genotypes in the four major racial groups are shown. F is the combined frequency over all three loci. $P^2$ is the match probability for the most common genotypes of all three loci combined. The combined F values ranged from $1.66*10^{-4}$ to $1.28*10^{-3}$. The frequencies of the least common genotypes were on the order of $10^{-16}$.

TABLE 5

Most Frequent Genotype at the Three STR Loci in Four Populations

| Locus | African Americans | Caucasians | Hispanics | Asians |
|---|---|---|---|---|
| D9S302 [GATA]$_n$ | 0.043 | 0.056 | 0.076 | 0.022 |
| D22S683 [GATA]$_n$ | 0.028 | 0.059 | 0.087 | 0.099 |
| D18S535 [GATA]$_n$ | 0.138 | 0.130 | 0.193 | 0.144 |
| Combined (F) | $1.66 * 10^{-4}$ | $4.29 * 10^{-4}$ | $1.28 * 10^{-3}$ | $3.14 * 10^{-4}$ |
| $P^2$ | $6.67 \times 10^{-6}$ | $2.25 \times 10^{-5}$ | $4.08 \times 10^{-5}$ | $1.76 \times 10^{-5}$ |

Many other variations and modifications may be made in the methods herein described, by those having experience in this art, without departing from the concept of the present invention. Accordingly, it should be clearly understood that the methods described in the foregoing description are illustrative only, and not intended as a limitation on the scope of the invention.

What is claimed is:

1. A method of DNA typing comprising multiplex amplifying the D18S535, D22S683 and D9S302 loci of DNA.

2. The method of claim 1, wherein the multiplex amplifying is performed with template DNA, magnesium and primers of SEQ. ID. NOS. 1, 2, 3,4, 5, and 6.

3. The method of claim 2, wherein the template DNA is about 0.05 to 0.5 ng/µl and the magnesium concentration is about 0.5 to 1.2 mM.

4. The method of claim 2, wherein the template DNA is about 0.2 ng/µl and the magnesium concentration is about 0.8 mM.

5. The method of claim 3, wherein the primer concentrations are about 0.1 to 1.0 µM.

6. The method of claim 4, wherein the primer concentrations are about 0.4 µM for SEQ. ID. NOS. 1, 2, 5 and 6, and about 0.6 µM for SEQ. ID. NOS. 3 and 4.

7. The method of claim 6 comprising the steps of:

a. an initial hold at about 94.5° C. for about 2.5 minutes;

b. about 30 cycles at about 95° C. for about ¾ minutes, about 58° C. for about 1 minute and about 72° C. for about 1 minute;

c. a hold of about 72° C. for about 7 minutes; and d. a final hold at about 15° C.

8. A method of DNA typing comprising multiplex amplifying at least two loci wherein at least one locus is selected from the group consisting of the D 18S535, D22S683 and D9S302 loci.

9. The method of claim 8, wherein primers for the D18S535 locus are SEQ. ID. NOS. 1 and 2, primers for the D22S683 locus are SEQ. ID. NOS. 3 and 4 and primers for the D9S302 locus are SEQ. ID. NOS. 5 and 6.

10. A method of DNA typing comprising multiplex amplifying two loci selected from the group consisting of the D18S535, D22S683 and D9S302 loci.

11. The method of claim 10, wherein primers for the D18S535 locus are SEQ. ID. NOS. 1 and 2, primers for the D22S683 locus are SEQ. ID. NOS. 3 and 4 and primers for the D9S302 locus are SEQ. ID. NOS. 5 and 6.

12. A method of DNA typing comprising multiplex amplifying complex tandem repeats, said complex tandem repeats having a heterozygosity of about 87% to 97% and a GATA motif.

13. The method of claim 12, wherein a multiplex amplification of three complex tandem repeats has an exclusionary power of 98.1% to 99.9%.

14. The method of claim 12, wherein the multiplex amplification of three complex tandem repeats has an exclusionary power of 99.9% to 99.99%.

15. The method of claim 12, wherein the multiplex amplification is for two or three loci.

16. The method as in claim 15, wherein the complex tandem repeats are selected from the group consisting of D9S302 and D22S683 loci.

17. The method as in claim 15, wherein the complex tandem repeats are selected from the group consisting of D9S302, D22S683, D7S1804, D2S1780, D3S2387 and D2S1326 loci.

18. The method of claim 16, wherein primers for the D22S683 locus are SEQ. ID. NOS. 3 and 4 and primers for the D9S302 locus are SEQ. ID. NOS. 5 and 6.

19. An allelic ladder for use in DNA typing, said ladder comprising:

at least 8 alleles from at least one locus selected from the group consisting of a D9S302 locus, a D18S535 locus and a D22S683 locus.

20. The allelic ladder of claim 19, having at least 18 alleles from the D9S302 locus;

at least 10 alleles from the D18S535 locus; and at least 12 alleles from the D22S683 locus.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:1:

TCATGTGACA AAAGCCACAC                                       20

(2) INFORMATION FOR SEQ ID NO:2:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:2:

AGACAGAAAT ATAGATGAGA ATGCA                                25

(2) INFORMATION FOR SEQ ID NO:3:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:3:

AACAAAACAA AACAAAACAA ACA                                  23

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Genomic DNA

```
        (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:4:

GGTGGAAATG CCTCATGTAG                                              20

(2) INFORMATION FOR SEQ ID NO:5:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:5:

GGGGACAGAC TCCAGATACC                                              20

(2) INFORMATION FOR SEQ ID NO:6:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:6:

GCGACAGAGT GAAACCTTGT                                              20
```